United States Patent
Tsubouchi et al.

(10) Patent No.: US 10,405,840 B2
(45) Date of Patent: Sep. 10, 2019

(54) SURGICAL FIXING TOOL

(71) Applicant: TERUMO KABUSHIKI KAISHA, Tokyo (JP)

(72) Inventors: Takeshi Tsubouchi, Kanagawa (JP); Masamichi Yanai, Yasu (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 376 days.

(21) Appl. No.: 15/190,331

(22) Filed: Jun. 23, 2016

(65) Prior Publication Data

US 2017/0020502 A1 Jan. 26, 2017

(30) Foreign Application Priority Data

Jul. 21, 2015 (JP) ................................. 2015-144084

(51) Int. Cl.
*A61B 17/02* (2006.01)
*A61B 90/50* (2016.01)
(Continued)

(52) U.S. Cl.
CPC .............. *A61B 17/02* (2013.01); *A61B 90/50* (2016.02); *A61B 2017/00017* (2013.01); *A61B 2017/00057* (2013.01); *A61B 2017/00539* (2013.01); *A61B 2017/00703* (2013.01); *A61B 2017/00876* (2013.01); *A61B 2017/0237* (2013.01); *A61B 2017/0243* (2013.01); *A61B 2017/1107* (2013.01); *A61B 2017/306* (2013.01);
(Continued)

(58) Field of Classification Search
CPC ..................... A61B 2017/00243–00256; A61B 2017/00561; A61B 2017/00703; A61B 2017/0243; A61B 2017/0237; A61B 17/02; A61B 2017/306–308
USPC .......................................................... 600/37
See application file for complete search history.

(56) References Cited

U.S. PATENT DOCUMENTS

| 5,836,311 A | 11/1998 | Borst et al. |
| 6,368,332 B1 * | 4/2002 | Salcudean ............... A61B 90/50 |
| | | 128/897 |

(Continued)

FOREIGN PATENT DOCUMENTS

| WO | 2008107593 A2 | 9/2008 | |
| WO | WO-2008107593 A2 * | 9/2008 | ............. A61B 17/02 |
| WO | WO 2008107593 A2 * | 9/2008 | ............. A61B 17/02 |

OTHER PUBLICATIONS

European Search Report dated Sep. 13, 2016, Serial No. 16170555.3.

(Continued)

*Primary Examiner* — Catherine B Kuhlman
(74) *Attorney, Agent, or Firm* — MacMillan, Sobanski & Todd, LLC

(57) ABSTRACT

A surgical fixing tool for vascular anastomosis inhibits an operation site on a surface of a living body such as a heart from moving along a height direction of the surface of the living body. The fixing tool has a position adjusting unit disposed in a support unit 10 that adjusts a relative position between the support unit and the fixed living body local site. A displacement position detection unit detects a displacement position of a local site. Based on a detected displacement, the position adjusting unit changes and adjusts a relative position between the support unit and the fixed local site.

5 Claims, 9 Drawing Sheets

(51) Int. Cl.

| | |
|---|---|
| *A61B 17/00* | (2006.01) |
| *A61B 17/11* | (2006.01) |
| *A61B 90/00* | (2016.01) |
| *A61B 17/30* | (2006.01) |
| *A61B 90/57* | (2016.01) |

(52) U.S. Cl.
CPC ... *A61B 2017/308* (2013.01); *A61B 2090/061* (2016.02); *A61B 2090/571* (2016.02)

(56) References Cited

U.S. PATENT DOCUMENTS

| | | |
|---|---|---|
| 8,753,266 B2 | 6/2014 | Spence et al. |
| 2002/0120177 A1 | 8/2002 | Borst et al. |
| 2003/0060685 A1 | 3/2003 | Houser et al. |
| 2004/0260145 A9 | 12/2004 | Borst et al. |
| 2007/0232865 A1* | 10/2007 | Efinger ............... A61B 17/02 |
| | | 600/227 |

OTHER PUBLICATIONS

Wael Bachta et al., "Active Stabilization for Robotized Beating Heart Surgery", IEEE Transactions on Robotics, IEEE Service Center, Piscataway, NJ, US, vol. 27, No. 4, Aug. 1, 2011 (Aug. 1, 2011), pp. 757-768.

Bebek O et al., "Intelligent Control Algorithms for Robotic-Assisted Beating Heart Surgery", IEEE Transactions on Robotics, IEEE Service Center, Piscataway, NJ, US, vol. 23, No. 3, Jun. 1, 2007 (Jun. 1, 2007), pp. 468-480.

* cited by examiner

SURGICAL FIXING TOOL

CROSS REFERENCE TO RELATED APPLICATIONS

This application claims priority to Japanese application no. 2015-144084, filed Jul. 21, 2015, which is incorporated herein by reference in its entirety.

TECHNICAL FIELD

The present invention relates to a surgical fixing tool used for an operative surgical procedure of a living body local site, for example, a surgical procedure of the living body such as an off-pump coronary artery bypass for treating stenocardia caused by coronary artery arctation or myocardial infarction.

BACKGROUND ART

An operative surgical procedure of a living body local site, for example, a coronary artery bypass, is a treatment method for increasing blood flowing to myocardia by newly performing a graft vascular anastomosis and connecting a bypass before a lesion appears in a stenosed coronary artery.

When the vascular anastomosis is performed using an on-pump coronary artery bypass, the anastomosis is performed by immobilizing a heart while an artificial cardiopulmonary device causes blood to flow into a patient. However, the coronary artery bypass performed by immobilizing the heart needs the artificial cardiopulmonary device which is expensive and bulky. In addition, if the artificial cardiopulmonary device is used, in some cases, inflammatory reaction occurring when the blood passes through the inside of a circuit of the artificial cardiopulmonary device imposes a strain on a patient's body, thereby causing various disadvantages. Therefore, an off-pump coronary artery bypass (OPCAB) is sometimes performed in place of the on-pump coronary artery bypass.

In the off-pump coronary artery bypass, the vascular anastomosis is performed in a state where the heart beats. During this procedure, since the heart is in a beating state, the vascular anastomosis becomes difficult. Accordingly, a specialized tool may be used as disclosed in U.S. Pat. No. 5,836,311.

For this specialized tool, a surgical fixing tool called a stabilizer is used. This stabilizer is a tool which is attached to a heart outer surface by means of suction so as to facilitate the vascular anastomosis in an operation target site at a central position of a peripheral portion after inhibiting movements of a peripheral portion on the heart surface fixed by the suction.

SUMMARY OF INVENTION

Technical Problem

When a surgical fixing tool in the related art is used, even when a heart beats, it is possible to inhibit movements of a peripheral portion on a heart surface. However, an operation target site at a central position in the peripheral portion of the heart surface inevitably moves along a height direction (perpendicular direction) of the heart surface in response to heartbeats. Consequently, it remains to be challenging for an operator or a skilled person to perform vascular anastomosis for the operation site on the heart surface.

Therefore, the present invention aims to provide a surgical fixing tool which can easily and reliably perform treatment such as vascular anastomosis by inhibiting an operation site on a surface of a living body such as a heart and the like from moving along a height direction of the surface of the living body in response to movements of the living body.

Solution to Problem

According to the present invention, there is provided a surgical fixing tool including a support unit which exposes an area required for a living body local site subjected to an operative procedure or operative skill and which surrounds at least a portion of the local site so as to be contacted and fixed thereto. The surgical fixing tool includes a position adjusting unit that is disposed in the support unit, and that adjusts a relative position between the support unit and the fixed living body local site, and a displacement position detection unit that detects a displacement position where the living body local site is displaced in a height direction, based on movements of the living body. Based on a detection result of the displacement position in the height direction of the living body local site which is detected by the displacement position detection unit, the position adjusting unit changes the relative position between the support unit and the fixed living body local site so as to inhibit a position change in the height direction of the living body local site.

According to the above-described configuration, the support unit circumscribes the area required for the living body local site, and surrounds at least the portion of the local site so as to be attached and fixed thereto. Based on the detection result of the displacement position in the height direction of the living body local site which is detected by the displacement position detection unit, the position adjusting unit changes the relative position between the support unit and the fixed living body local site so as to inhibit the position change in the height direction of the living body local site. In this manner, in a state where a peripheral portion on a surface of the living body such as a heart and the like is fixed by the support unit, an operation site at a central position of the peripheral portion on the surface of the living body such as the heart and the like is inhibited from relative movement along the height direction of the surface of the living body in response to movements of the living body. Accordingly, it is possible to easily and reliably perform treatment such as vascular anastomosis.

Preferably, the support unit provides a frame which has an opening portion for exposing the living body local site. The support unit has a fixing base, a fixing arm which holds a position of the fixing base with respect to a fixed body, and a movable suction unit which has a suction pad held in a lower portion of the fixing base so as to perform suction on a surface of the living body, and the suction pad is connected to a negative pressure generation unit which generates negative pressure for the suction pad.

According to the above-describe configuration, the support unit exposes the living body local site through the opening portion so as to hold the position of the fixing base by using the fixing arm which attaches to the fixed body. The movable suction unit applies suction on the surface of the living body by using the suction pad held in the lower portion of the fixing base. Therefore, while the support unit holds the fixed body via the fixing arm in a state where the support unit is positioned on the surface of the living body, the suction pad of the movable suction unit can perform the suction in a state where the surface of the living body is stabilized.

Preferably, the position adjusting unit has an actuator member and a drive unit which feeds a hydraulic fluid to the actuator member. The actuator member is disposed between the fixing base and the movable suction unit. The drive unit of the hydraulic fluid applies pressure generated by the hydraulic fluid into the actuator member so as to adjust the relative position between the fixing base of the support unit and the fixed living body local site by changing (e.g., extending or retracting a position of the movable suction unit with respect to the fixing base of the support unit.

According to the above-describe configuration, the drive unit of the hydraulic fluid applies the pressure generated by the hydraulic fluid into the actuator member so as to adjust the relative position between the fixing base of the support unit and the fixed living body local site by changing the position of the movable suction unit with respect to the fixing base. Therefore, the position of the movable suction unit with respect to the fixing base is changed so as to push the living body in a direction and distance opposed to the displacement caused by the heartbeat. In this manner, it is possible to easily and reliably adjust the relative position between the fixing base and the fixed living body local site.

Preferably, the displacement position detection unit is attached to the fixing base. The displacement position detection unit emits light to the living body local site exposed inside the support unit so as to measure a distance between the fixing base and the living body local site. After comparing the actual measurement distance obtained from the displacement position detection unit and a predetermined target distance with each other, the drive unit of the hydraulic fluid applies the pressure generated by the hydraulic fluid into the actuator member so that the actual measurement distance becomes the target distance, and accordingly the relative position is adjusted between the fixing base of the support unit and the fixed living body local site by changing the position of the movable suction unit with respect to the fixing base of the support unit.

According to the above-describe configuration, the actual measurement distance between the fixing base of the support unit and the living body local site can be accurately obtained in a contactless manner, only by emitting the light to the living body local site from the displacement position detection unit. The position of the movable suction unit with respect to the fixing base is changed so that the actual measurement distance becomes the target distance. In this manner, it is possible to easily and reliably adjust the relative position between the fixing base and the fixed living body local site.

Preferably, the suction pad and the negative pressure generation unit are detachably connected to each other, and the actuator member and the drive unit are detachably connected to each other. According to this configuration, the suction pad of the support unit and the negative pressure generation unit are detachable, and the actuator member of the support unit and the drive unit are detachable. Accordingly, from a viewpoint of hygiene, the support unit used for an operative procedure can be detached from the negative pressure generation unit and the drive unit. Therefore, a new support unit can be attached and used for the subsequent operative procedure.

Preferably, the fixed body is a part of an operating table which holds the living body during the surgical procedure. For example, the fixing base of the support unit may be fixed to the part of the operating table by utilizing the part of the operating table. In this manner, the fixing base of the support unit can reliably hold a patient's living body local site so as not to move.

Preferably, a shape of the support unit is any one of a U-shape, a V-shape, a substantially circular shape including an elliptical shape and an oval shape, and a polygonal shape.

According to the above-describe configuration, in accordance with a shape of the living body or a shape of the operation target site, the shape of the support unit can employ any one of the U-shape, the V-shape, the circular shape, and the polygonal shape.

Advantageous Effects of Invention

According to the present invention, it is possible to provide a surgical fixing tool which can easily and reliably perform treatment such as vascular anastomosis by inhibiting an operation site on a surface of a living body such as a heart and the like from moving along a height direction of the surface of the living body in response to movements of the living body.

DESCRIPTION OF PREFERRED EMBODIMENTS

Hereinafter, preferred embodiments according to the present invention will be described in detail with reference to the drawings. The embodiments described below are preferable specific examples of the present invention, and thus, have various technically preferred limitations imposed thereon. However, the scope of the present invention is not limited to these embodiments as long as the following description has no particular intent that the present invention is limited.

First Embodiment

Figure 1:
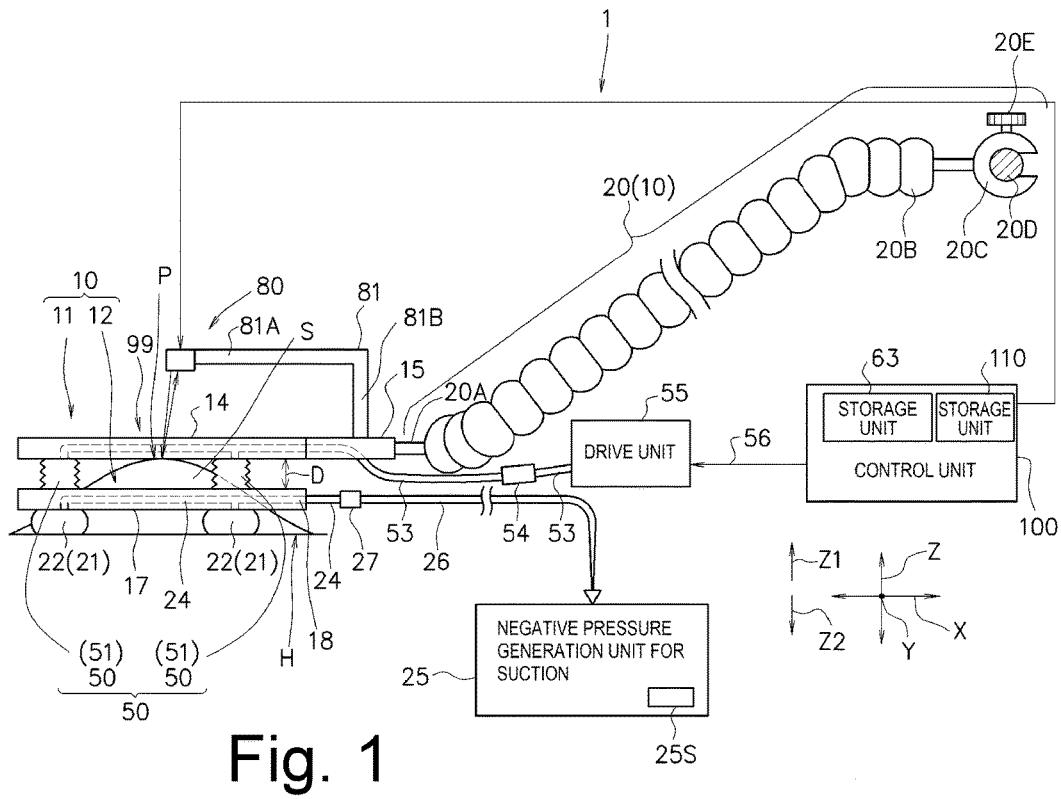
FIG. 1 is an overall system diagram illustrating a surgical fixing tool according to a first preferred embodiment of the present invention.
Figure 2:
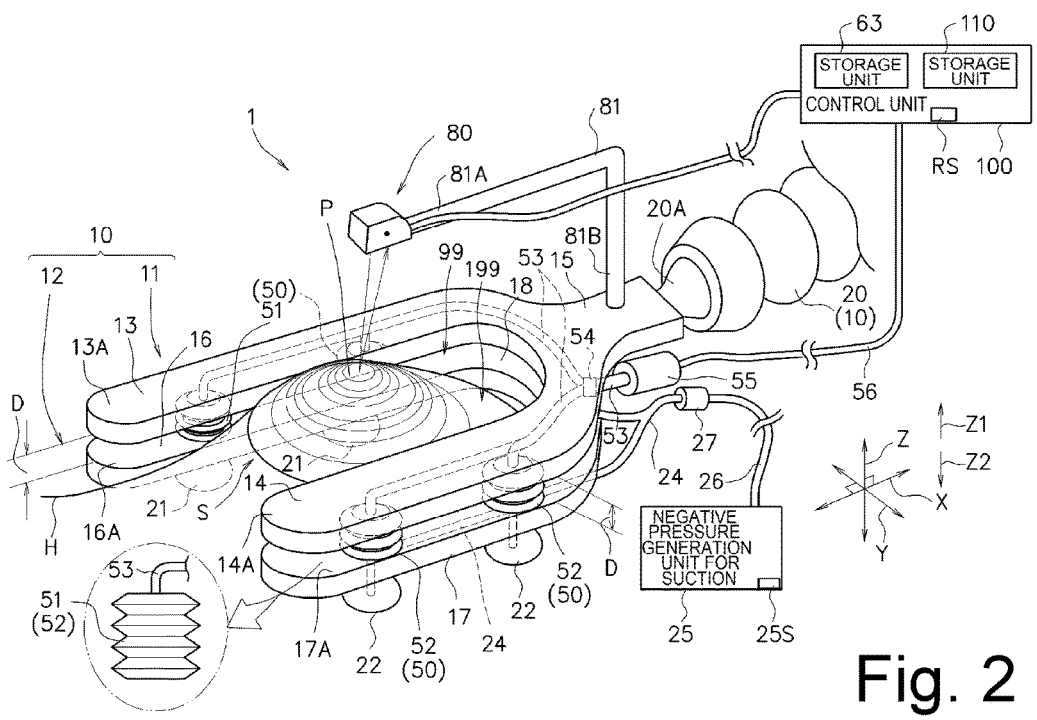
FIG. 2 is a perspective view in which a structure of the surgical fixing tool illustrated in FIG. 1 is illustrated in more detail.

FIG. 1 is an overall system diagram illustrating a surgical fixing tool according to a first preferred embodiment of the present invention. FIG. 2 is a perspective view in which a structure of the surgical fixing tool illustrated in FIG. 1 is illustrated in more detail.

A surgical fixing tool 1 illustrated in FIGS. 1 and 2 is used when an off-pump coronary artery bypass is performed on a heart H, for example, as a living body local site of a patient subjected to an operative procedure or operative skill. With regard to a local site P on a surface S of the heart H, the surgical fixing tool 1 is used when an area region required for the surface S of the heart H is exposed and at least a portion of the local site on the surface S of the heart H is surrounded, attached, and fixed so as to inhibit a position change in a height direction (direction Z) of the local site P on the surface S of the heart H. The local site P on the surface S of the heart H corresponds to an operation target site of the off-pump coronary artery bypass. The surgical fixing tool 1 can also be called a stabilizer, a surgical fixing treatment tool, a surgical fixing treatment device, or the like.

As illustrated in FIGS. 1 and 2, the surgical fixing tool 1 generally has a support unit 10, a position adjusting unit 50, a displacement position detection unit 80, a control unit 100, and the like. The support unit 10 exposes a required area in a region including the local site P on the surface S of the heart H and surrounds at least a portion of the local site P on the surface S of the heart H so as to be attached and fixed to the surface S of the heart H. The support unit 10 has a fixing base 11, a movable suction unit 12, and a fixing arm 20. The fixing base 11 and the movable suction unit 12 have substantially the same size, and are preferably formed in a substantially U-shape. The fixing base 11 and the movable suction unit 12 are made of stainless steel or titanium, for example, or other metal which can ensure the strength for attaching and fixing the surface S of the heart H and moreover which has excellently biocompatibility for the living body.

As illustrated in FIG. 2, the fixing base 11 has a first arm 13, a second arm 14, and an extension portion 15. A front end portion 13A of the first arm 13 and a front end portion 14A of the second arm 14 terminate with a substantially semicircular shape. Preferably, all edges of the first arm 13 and the second arm 14 are also configured to be rounded chamfered so as not to erroneously damage the surface S of the heart H. In this manner, it is possible to arrange the front end portion 13A of the first arm 13 and the front end portion 14A of the second arm 14 so as not to erroneously damage the surface S of the heart H. The extension portion 15 is formed so as to extend from a rear end portion of the first arm 13 and a rear end portion of the second arm 14.

An opening portion 99 is formed between the first arm 13 and the second arm 14 of the fixing base 11. The opening portion 99 exposes a region of a fixed area including the local site P on the surface S of the heart H to provide access for performing anastomosis and for measuring displacement.

The fixing arm 20 illustrated in FIGS. 1 and 2 fixes a position of the fixing base 11 so that the fixing base 11 does not move, and for example, the fixing arm 20 is a member for fixing the position to a rail 20D of an operating table as illustrated in FIG. 1. The rail 20D of the operating table is an example of a fixed body for holding and fixing the position of the fixing base 11 to the heart H. That is, the position of the fixing base 11 of the support unit 10 is held in the rail 20D of the operating table, for example, by using the fixing arm 20 so that the position does not move from the heart H which is the living body. The position of the fixing arm 20 fixes the fixing base 11 so as not to move in a direction Z (direction perpendicular to a heart wall of the heart H, height direction), a direction X, and a direction Y. In this manner, the fixing base 11 of the support unit 10 can easily and reliably fix the surface S of the heart H so as not to move.

The fixing arm 20 illustrated in FIGS. 1 and 2 is a metal-made member having a deformable bellows shape. An operator or a skilled person can freely bend the fixing arm 20 so as to maintain a required shape. Moreover, as illustrated in FIG. 1, one end portion 20A of the fixing arm 20 is detachably connected to the extension portion 15. In this manner, the fixing base 11 of the support unit 10 can be detached and replaced from one end portion 20A of the fixing arm 20 for each new operative procedure.

As illustrated in FIG. 1, the other end portion 20B of the fixing arm 20 has an interlock portion 20C. For example, the interlock portion 20C can be fixed so as to be detachable from the rail 20D of the operating table on which a patient lies, for example, by turning a fixing screw 20E. In this manner, as illustrated in FIGS. 1 and 2, an operator or a skilled person can freely bend the fixing arm 20 so as to maintain a state where a unit of the fixing base 11 and the movable suction unit 12 are properly brought into contact with the surface S of the heart H by utilizing the rail 20D of the operating table.

As illustrated in FIGS. 1 and 2, the movable suction unit 12 is arranged in parallel at a position below the fixing base 11 by leaving a predetermined distance therebetween. As illustrated in FIG. 2, the movable suction unit 12 has a first arm 16, a second arm 17, and an arcuate portion 18. A front end portion 16A of the first arm 16 and a front end portion 17A of the second arm 17 are formed round in a substantially semicircular shape. In this manner, it is possible to arrange the front end portion 16A of the first arm 16 and the front end portion 17A of the second arm 17 so as not to erroneously damage the surface S of the heart H. The arcuate portion 18 connects a rear end portion of the first arm 16 and a rear end portion of the second arm 17 to each other.

As illustrated in FIG. 2, the movable suction unit 12 has an opening portion 199 for exposing a region of a fixed area on the surface S of the heart H. The opening portion 199 of the movable suction unit 12 has the same size as the opening portion 99 of the fixing base 11, and the region of the fixed area including the local site P on the surface of the heart H can be exposed through the opening portions 99 and 199.

Next, a plurality of suction pads 21 and 22 disposed in the movable suction unit 12 will be described.

Figure 3:
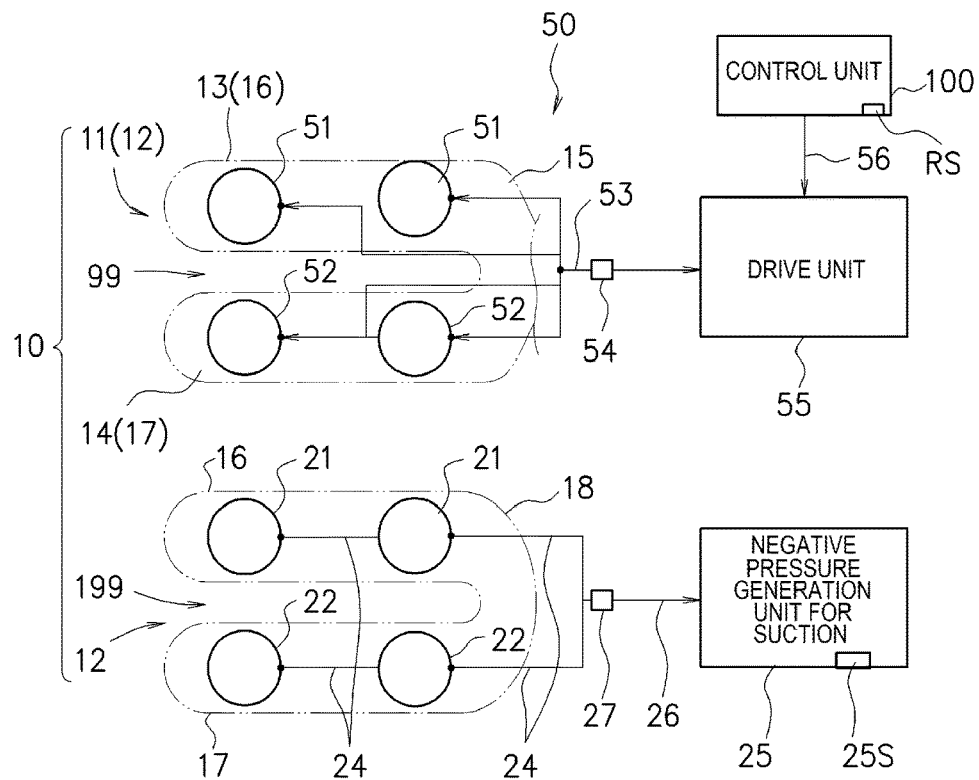
FIG. 3 is a view illustrating a structure example in which a plurality of actuator chambers are connected and a structure example in which a plurality of suction pads are connected.

FIG. 3 is a view illustrating a structure example in which a plurality of actuator chambers 51 and 52 as actuator members are connected and a structure example in which a plurality of the suction pads 21 and 22 are connected. As previously described, the fixing base 11 having the substantially U-shape illustrated in FIG. 3 has the first arm 13, the second arm 14, and the extension portion 15, and forms the opening portion 99. Similarly, the movable suction unit 12 having the substantially U-shape has the first arm 16, the second arm 17, and the arcuate portion 18, and forms the opening portion 199.

As illustrated in FIGS. 1 to 3, the movable suction unit 12 has a plurality of suction pads, for example, four suction pads 21 and 22 in total. As illustrated in FIG. 2, two suction pads 21 are disposed on a lower surface side of the first arm 16 by leaving a predetermined distance therebetween. Similarly, another two suction pads 22 are disposed on a lower surface side of the second arm 17 by leaving a predetermined distance therebetween, facing suction pads 21. As illustrated in FIG. 1, each upper end portion of the four suction pads 21 and 22 is fixed to a lower surface side of the first arm 16 or a lower surface side of the second arm 17. Each lower end portion of the four suction pads 21 and 22 is a portion which is in close contact with a peripheral portion of the local site P on the surface S of the heart H. The four suction pads 21 and 22 are elastically deformable, and are made of a flexible and plastic material which does not adversely affect a living body, for example, such as vinyl chloride, polyurethane, silicone rubber, and the like.

As illustrated in FIGS. 2 and 3, the four suction pads 21 and 22 have substantially the same size and are connected to a negative pressure generation unit 25 via conduits 24 and 26. The conduit 24 is arranged inside the first arm 16 and the second arm 17, and has a connection terminal 27. As illustrated in FIG. 3, one end portion of the conduit 26 is detachably connected to a connection terminal 27, and the other end portion of the conduit 26 is connected to the negative pressure generation unit for suction 25.

The negative pressure generation unit for suction 25 illustrated in FIG. 3 has a starting switch 25S. An operator or a skilled person pushes the starting switch 25S, thereby causing the negative pressure generation unit for suction 25 to perform air suction from the inside of the four suction pads 21 and 22 via the conduits 26 and 24. In this manner, the support unit 10 including the movable suction unit 12 and the fixing base 11 which are illustrated in FIG. 2 can be fixed to a peripheral portion on the surface S of the heart H subjected to an operative procedure or operative skill, through the air suction using negative pressure.

Next, the position adjusting unit 50 will be described with reference to FIGS. 1 to 3.

The position adjusting unit 50 illustrated in FIGS. 1 and 2 is attached between the fixing base 11 and the movable suction unit 12 of the support unit 10. The position adjusting unit 50 adjusts a relative position between the fixing base 11 of the support unit 10 and the local site P on the surface S of the heart H in such a way that the movable suction unit 12 is lowered in a direction Z2 by extending the length in the direction Z and the surface S of the heart H is pushed in the direction Z2.

As illustrated in FIG. 3, for example, the position adjusting unit 50 has four actuator chambers 51 and 52, as a plurality of actuator members, and a conduit 53. The conduit 53 is connected to a drive unit 55. The drive unit 55 is electrically connected to the control unit 100 by an electric wire 56.

As illustrated in FIGS. 1 and 2, each upper end portion of the two actuator chambers 51 and 51 is fixed to the lower surface of the first arm 13, and each lower end portion of the two actuator chambers 51 and 51 is fixed to the upper surface of the first arm 16. Similarly, each upper end portion of another two actuator chambers 52 and 52 is fixed to the lower surface of the second arm 14, and each lower end portion of the two actuator chambers 52 and 52 is fixed to the upper surface of the second arm 17. The actuator chambers 51 and 52 are bellow-shaped members which are elastically deformable, and are made of metal or a plastic material which is flexible and which does not affect a living body, for example, such as stainless steel, vinyl chloride, polyurethane, polypropylene, synthetic rubber, and the like.

As illustrated in FIGS. 1 and 2, more preferably, each position of the two actuator chambers 51 corresponds to each position of the two suction pads 21 in the direction Z (height direction of the surface S of the heart H). Each position of the two actuator chambers 52 corresponds to each position of the two suction pads 22 in the direction Z (height direction of the surface S of the heart H).

As illustrated in FIGS. 2 and 3, the four actuator chambers 51 and 52 are connected to the drive unit 55 via the conduit 53. A connection terminal 54 is preferably arranged in an intermediate portion of the conduit 53. When the support unit 10 is replaced, the drive unit 55 can be separated from the four actuator chambers 51 and 52 side by detaching the conduit 53 from the connection terminal 54.

Figure 4:
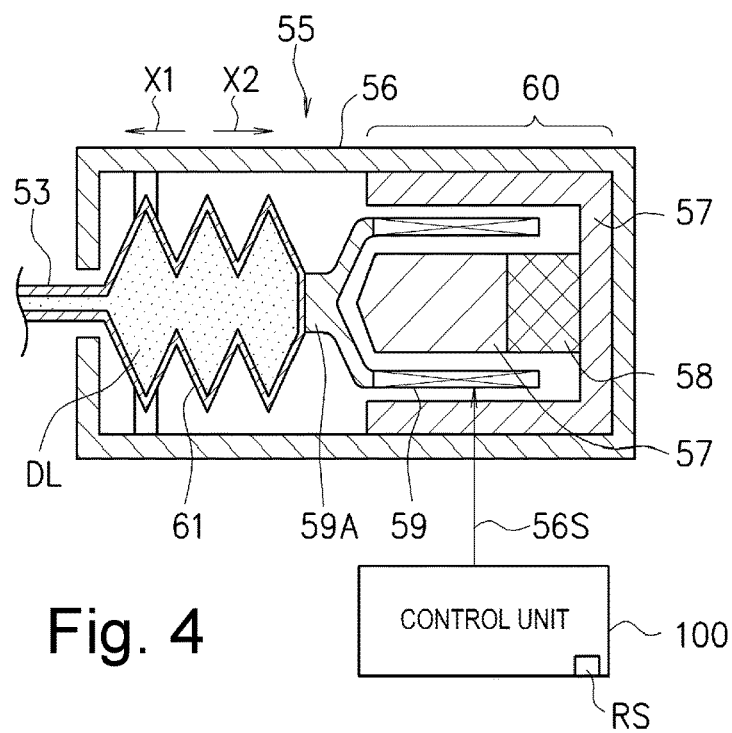
FIG. 4 is a sectional view illustrating a preferred structure example of a drive unit illustrated in FIGS. 1 to 3.

FIG. 4 is a sectional view illustrating a preferred structure example of the drive unit 55 illustrated in FIGS. 1 to 3. The drive unit 55 illustrated in FIG. 4 is a hydraulic fluid drive source for increasing pressure of a hydraulic fluid DL inside the four actuator chambers 51 and 52 by feeding the hydraulic fluid DL to the four actuator chambers 51 and 52 illustrated in FIG. 3 through the conduit 53. The drive unit 55 has a case 56, a voice coil motor 60, and an actuator cylinder 61 whose length is extendable. The case 56 accommodates the voice coil motor 60 and the actuator cylinder 61. The voice coil motor 60 has a core 57, a magnet 58, and a drive coil 59. The drive coil 59 is electrically connected to the control unit 100 via an electric wire 56S.

The actuator cylinder 61 is elastically deformable along a direction X1 and a direction X2, and is made of a flexible metal or plastic material, for example, such as vinyl chloride, polyurethane, acrylonitrile butadiene styrene (ABS), synthetic rubber, and the like.

As illustrated in FIG. 4, one end portion of the actuator cylinder 61 is connected to the conduit 53, and the other end portion of the actuator cylinder 61 is fixed to an attachment portion 59A of the drive coil 59. The inside of the actuator cylinder 61 is filled with the hydraulic fluid DL as a hydraulic fluid to be fed to the four actuator chambers 51 and 52 through the conduit 53. As the hydraulic fluid DL, it is possible to employ hydraulic oil or the like, for example. According to this configuration, the control unit 100 supplies power to the drive coil 59 through the electric wire 56S, thereby causing interaction between a magnetic field generated by the drive coil 59 and a magnetic field of the magnet 58. In this manner, the actuator cylinder 61 can contract in the direction X1, and can extend in the direction X2.

If the actuator cylinder 61 illustrated in FIG. 4 contracts in the direction X1, pressure of the hydraulic fluid DL to be fed to the four actuator chambers 51 and 52 via the conduit 53 increases. This causes the four actuator chambers 51 and 52 illustrated in FIGS. 1 and 2 to extend in the direction Z2 (downward direction in FIG. 1). Therefore, it is possible to widen a distance D of the movable suction unit 12 downward in the direction Z2 from the fixing base 11 whose position is fixed.

On the other hand, if the actuator cylinder 61 illustrated in FIG. 4 extends in the direction X2, the pressure of the hydraulic fluid DL to be fed to the four actuator chambers 51 and 52 via the conduit 53 decreases. This causes the four actuator chambers 51 and 52 to contract in the direction Z1. Therefore, it is possible to narrow the distance D between the fixing base 11 illustrated in FIGS. 1 and 2 and the movable suction unit 12.

Figure 5:
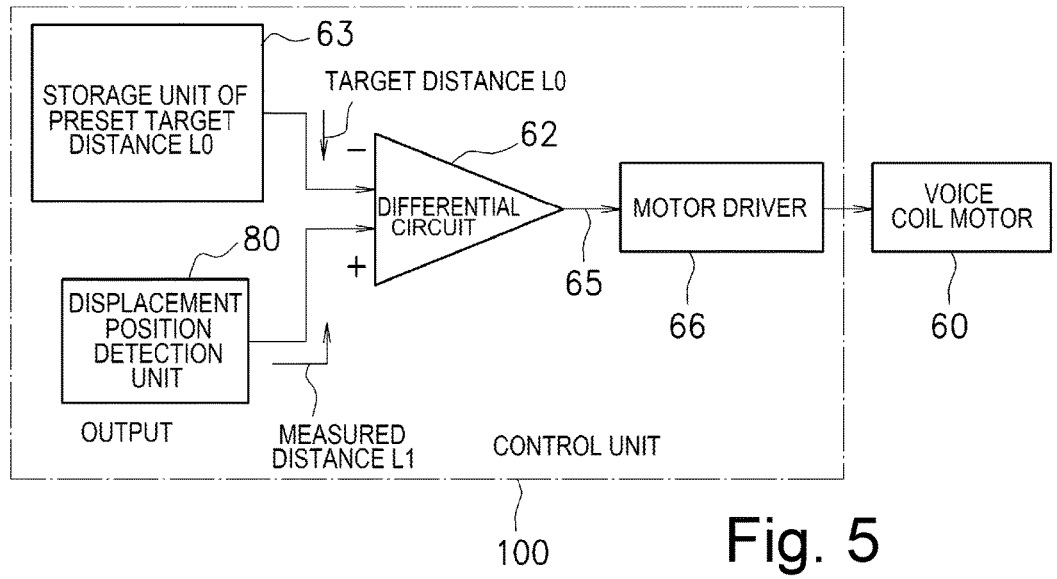
FIG. 5 is a view illustrating a drive circuit example of a control unit for driving a voice coil motor illustrated in FIG. 4.

FIG. 5 is a view illustrating a drive circuit example of the control unit 100 for driving the voice coil motor 60 illustrated in FIG. 4. As illustrated in FIG. 5, a previously determined target distance L0 is preset in a presetting memory 63. A differential circuit 62 is electrically connected to the presetting memory 63 and the displacement position detection unit 80. The differential circuit 62 can calculate a differential value 65 by obtaining a difference between the target distance L0 preset from the presetting memory 63 and an actual measurement distance L1 which is a detection output value of a distance actually measured by the displacement position detection unit 80. Then, in the differential circuit 62, based on the differential value 65, a motor driver 66 supplies power to the drive coil 59 illustrated in FIG. 4 in the voice coil motor 60. In this manner, the actuator cylinder 61 applies pressure to the hydraulic fluid DL inside the four actuator chambers 51 and 52.

In this manner, although details will be described later, the control unit 100 can adjust the actual measurement distance L1 between the displacement position detection unit 80 and the local site P protruding on the surface S of the heart H to the predetermined target distance L0 by using the drive unit 55 and the four actuator chambers 51 and 52.

As described above, the four actuator chambers 51 and 52 of the position adjusting unit 50 are arranged between the fixing base 11 and the movable suction unit 12 of the support unit 10. In this manner, since the pressure of the hydraulic fluid DL to be fed from the drive unit 55 increases, pressing force to be applied from the support unit 10 to the surface S of the heart H is adjusted and increased. Accordingly, the actual measurement distance L1 between the displacement position detection unit 80 and the local site P protruding on the surface S of the heart H can be accurately corrected to the predetermined distance L0.

Figure 6:
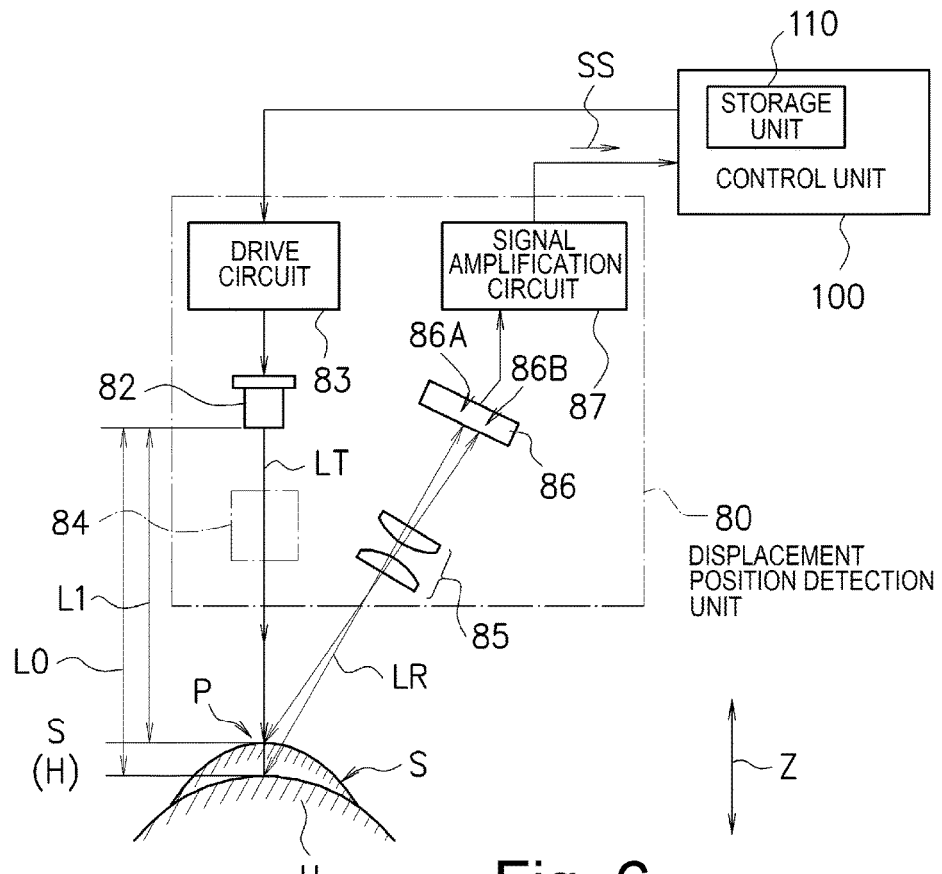
FIG. 6 is a view illustrating a configuration example of a displacement position detection unit.

Next, the displacement position detection unit 80 illustrated in FIGS. 1 and 2 will be described with reference to FIG. 6. FIG. 6 illustrates a configuration example of the displacement position detection unit 80. For example, as the displacement position detection unit 80, a laser displacement sensor of a triangulation system using laser light is used. The displacement position detection unit 80 detects a position displaced in the height direction (direction Z) of the local site P on the surface S by the heartbeats of the heart H in a contactless manner. A specific structure example of the displacement position detection unit 80 will be described.

As illustrated in FIGS. 1 and 2, the displacement position detection unit 80 is fixed to one end portion 81A of an L-shaped support member 81, for example. The other end portion 81B of the support member 81 is fixed to the extension portion 15. The displacement position detection unit 80 is located at an upper position of the local site P so as to correspond to the local site P on the surface S of the heart H located in the U-shaped support unit 10.

As illustrated in FIG. 6, the displacement position detection unit 80 preferably has a semiconductor laser 82, a drive circuit 83, a light projecting lens 84, a light receiving lens 85, a position sensitive detector (PSD) 86, and a signal amplification circuit 87. A distance between the semiconductor laser 82 of the displacement position detection unit 80 and the local site P on the surface S of the heart H which is the measurement target is illustrated by the predetermined target distance L0 and the actual measurement distance L1. When the heart H does not dilate, the distance in the direction Z is the predetermined target distance L0. When the heart H dilates, the distance in the direction Z becomes the actual measurement distance L1. The direction Z is a direction perpendicular to the surface S of the heart H (vertical direction in FIG. 6).

If the drive circuit 83 operates the semiconductor laser 82 in accordance with an instruction of the control unit 100, laser light LT emitted by the semiconductor laser 82 is emitted to the local site P on the surface S of the heart H via the light projecting lens 84. Then, return light LR of the laser light LT reflected on the local site P on the surface S of the heart H is received by the position sensitive detector 86 via the light receiving lens 85.

As illustrated in FIG. 6, the return light LR reflected on a position of the predetermined target distance L0 is received at a light receiving position 86A of the position sensitive detector 86. In addition, the return light LR reflected on a position of the actual measurement distance L1 is received by a light receiving position 86B of the position sensitive detector 86. According to this configuration, the position sensitive detector 86 outputs different detection signals corresponding to the respective positions to the signal amplification circuit 87.

In this manner, a difference between the predetermined target distance L0 in the direction Z and the actual measurement distance L1 can be detected as different detection values by changing the positions such as the light receiving positions 86A and 86B in the position sensitive detector 86. The signal amplification circuit 87 amplifies the detection value at the light receiving positions 86A and 86B transmits a signal SS of the detection result relating to the displacement position at which the local site P on the surface S of the heart H is displaced in the direction Z (height direction), to the control unit 100. Then, based on the signal SS of the detection result using the displacement position detection unit 80, the control unit 100 extends the actuator chambers 51 and 52 of the position adjusting unit 50, thereby increasing the pressing force applied to the surface S of the heart H and inhibiting the position of the support unit 10 from being changed in the height direction (direction Z) of the local site P on the surface S of the heart H.

Next, referring to FIGS. 7 to 10, an operation example will be described in which a position in the height direction (direction Z) of the local site P on the surface S of the heart H is inhibited from being changed due to the protruding local site P, for example, when an off-pump coronary artery bypass is performed on the heart by using the surgical fixing tool 1 illustrated in FIGS. 1 and 2, in a case where the local site P of the operation site protrudes in the direction Z1 due to the dilated heart H during the heartbeats.

Figure 7:
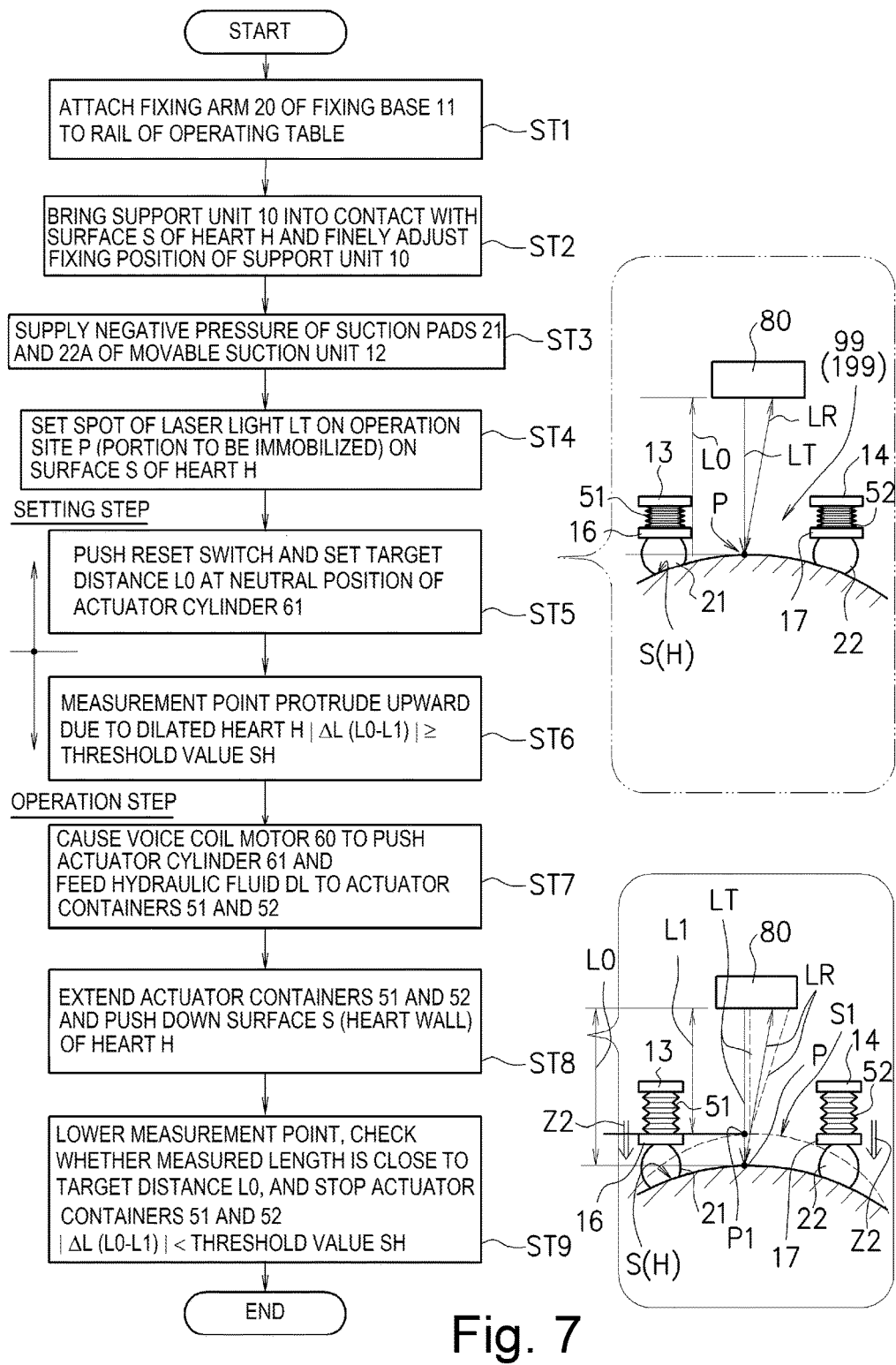
FIG. 7 is a flowchart illustrating an operation example of inhibiting a position change in a height direction (direction Z) of a local site P in the center on a surface S of a heart H when an off-pump coronary artery bypass is performed on the heart.
Figure 8:
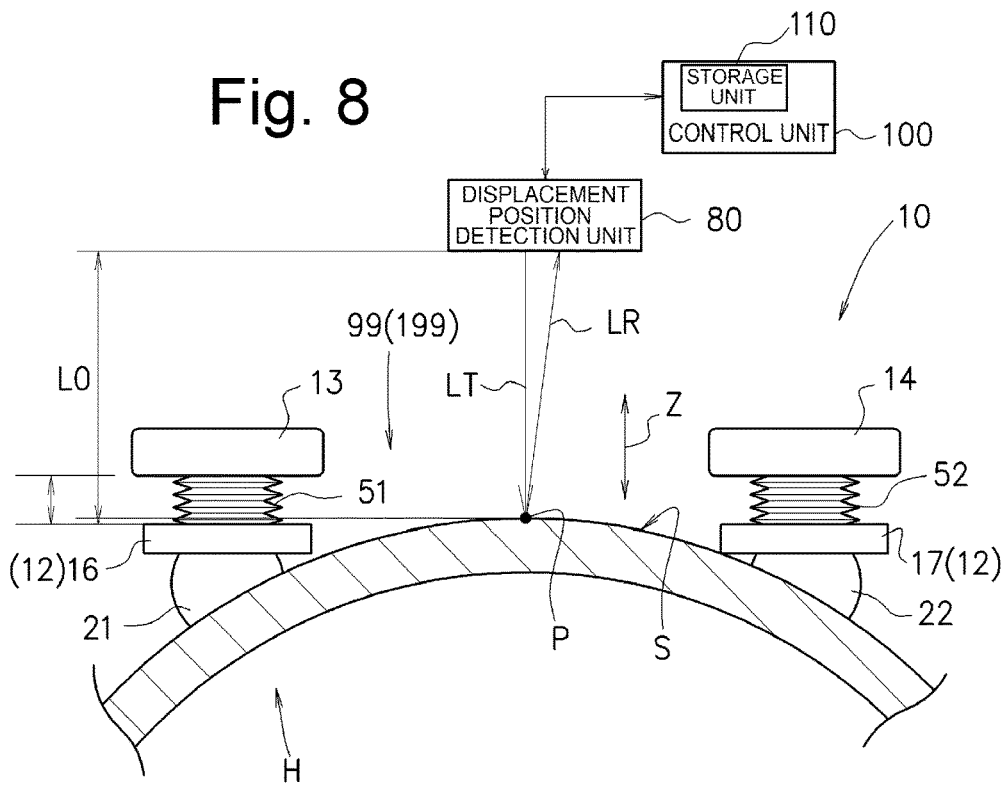
FIG. 8 is a view illustrating an example of a state where the heart H does not dilate.
Figure 9:
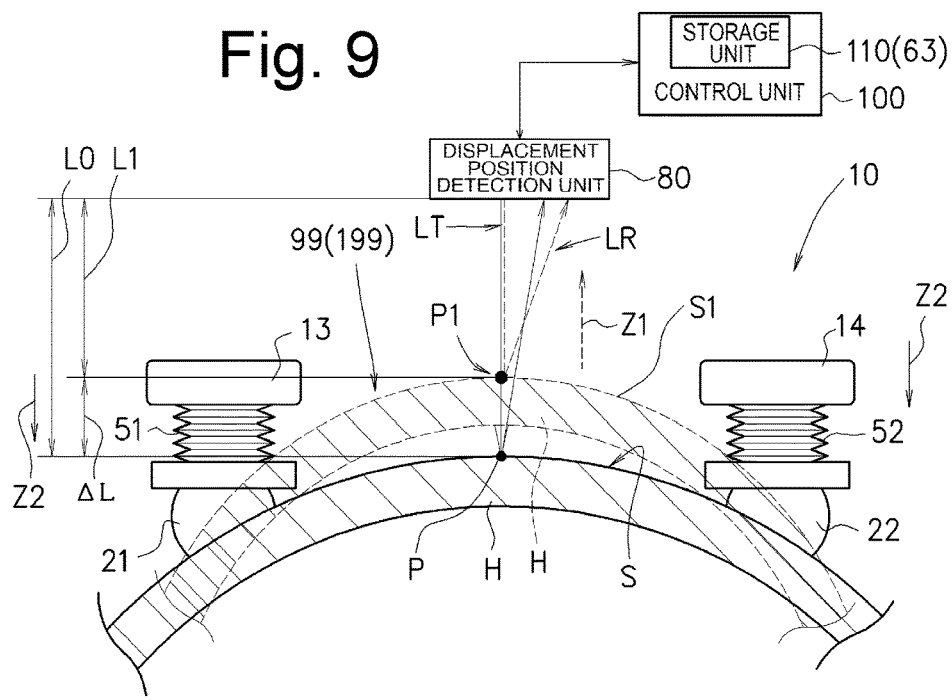
FIG. 9 is a view illustrating a state where the position change of the local site P in the center is inhibited when the heart H dilates.
Figure 10:
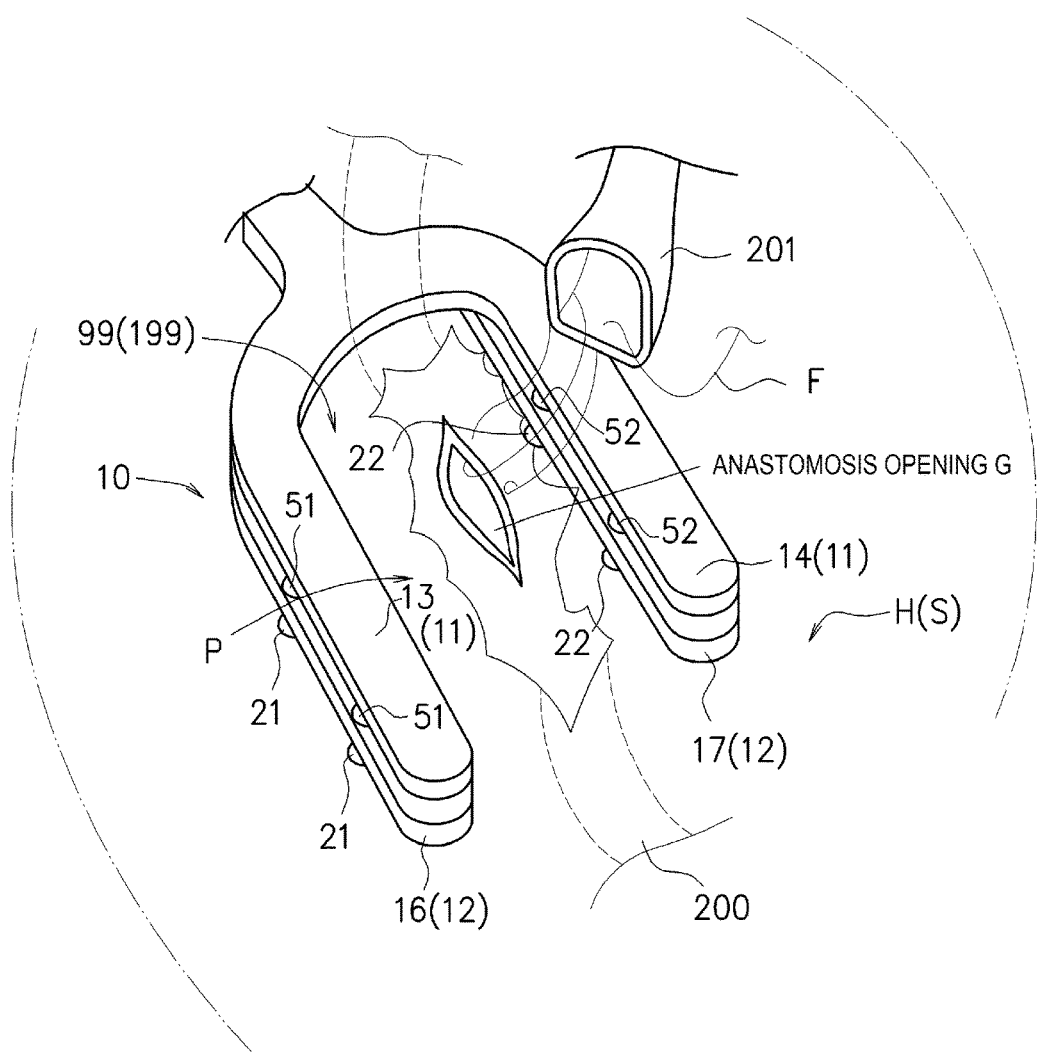
FIG. 10 is a view illustrating how a graft vessel for a bypass is newly connected to an anastomosis opening G opened in the local site P in the center of the heart H before a lesion appears in a stenosed coronary artery.

FIG. 7 is a flowchart illustrating the operation example of inhibiting the position change in the height direction (direction Z) of the local site P on the surface S of the heart H when the off-pump coronary artery bypass is performed on the heart. FIG. 8 illustrates an example of a state where the heart H does not dilate, and FIG. 9 is a view illustrating an example of a state where the position change of the local site P is inhibited when the heart H dilates. FIG. 10 is a view illustrating how a graft vessel for a bypass 201 is newly connected to an anastomosis opening G opened in the local site P of the heart H before a lesion appears in a stenosed coronary artery 200.

The flowchart illustrated in FIG. 7 has Step ST1 to Step ST9. As illustrated in FIG. 8, Step ST1 to Step ST5 correspond to a neutral position setting operation for support unit 10 on the heart H. In addition, Step ST6 to Step ST9 correspond to a movement-inhibiting operation for inhibiting the position change of the local site P when the heart H actually dilates.

As illustrated in FIG. 1, in Step ST1 in FIG. 7, the fixing arm 20 of the fixing base 11 of the support unit 10 is attached and fixed to the rail 20D of the operating table. In this manner, the position in the direction Z, the direction X, and the direction Y of the fixing base 11 of the support unit 10 can be reliably held with respect to the rail 20D by using the fixing arm 20. As illustrated in FIG. 8, the first arm 13 and the second arm 14 of the fixing base 11 of the support unit 10 is caused to face the surface S of the heart H so that the position is not changed.

As illustrated in FIG. 8, in Step ST2 in FIG. 7, an operator or a skilled person brings the four suction pads 21 and 22 of the support unit 10 into contact with the peripheral portion on the surface S of the heart H, and freely bends the fixing arm 20, thereby finely adjusting a position of the support unit 10 fixed to the surface S of the heart H. In this manner, the local site P of the operation site on the surface S of the heart H is located inside the opening portion 99 of the fixing arm 11 and the opening portion 199 of the movable suction unit 12. The suction pads 21 and 22 of the movable suction unit 11 of the support unit 10 perform suction on the peripheral portion of the local site P of the operation site on the surface S of the heart H.

In Step ST3 in FIG. 7, an operator or a skilled person pushes a starting switch 25S illustrated in FIG. 1, and drives the negative pressure generation unit for suction 25. The negative pressure generation unit for suction 25 supplies negative pressure of air to the four suction pads 21 and 22 of the movable suction unit 12 of the support unit 10 via the conduits 26 and 24. In this manner, the four suction pads 21 and 22 perform suction on the peripheral portion of the local site P on the surface S of the heart H as illustrated in FIG. 8. Accordingly, the support unit 10 is fixed to a correct position on the surface S of the heart H.

In Step ST4 in FIG. 7, the control unit 100 in FIG. 8 instructs the drive circuit 83 of the displacement position detection unit 80 illustrated in FIG. 6 so that the semiconductor laser 82 generates the laser light LT. The laser light LT is emitted to the local site P on the surface S of the heart H when the heart H does not dilate, thereby setting a spot of the laser light LT on the local site P of the operation site. In order that a bypass procedure can be facilitated during the bypass procedure, the local site P of the operation site has to be immobilized as much as possible by inhibiting an operation in which the local site P protrudes in the direction Z1 even when the heart H beats. In this case, a distance from the displacement position detection unit 80 to the local site P on the surface S of the heart H when the heart H does not dilate is stored in the storage unit 63 of the control unit 100 as the predetermined target distance L0. Thus, the target distance L0 is set as a neutral distance determined at a time when the heart H does not dilate.

In Step ST5 in FIG. 7, the operator or the skilled person pushes a reset switch RS of the control unit 100 illustrated in FIGS. 2 and 4 so as to transmit a reset signal to the drive unit 55 at the appropriate moment when the heart H is not dilated. In this manner, the control unit 100 sets the predetermined target distance L0 at a neutral position of the actuator cylinder 61.

In Step ST6 in FIG. 7, when the heart H illustrated in FIG. 9 beats and dilates, the dilating operation of the heart H causes the position of the local site P at a measurement point to protrude by a rising amount ΔL in the direction Z1 as illustrated in a local site P1 on a surface S1 of the heart H when the heart H dilates as illustrated by a broken line, compared to the surface S of the heart H when the heart H does not dilate as illustrated by a solid line. As illustrated by the broken line, when the heart H dilates and the local site P1 on the surface S1 of the dilated heart H rises by the rising amount ΔL, a distance between the displacement position detection unit 80 and the local site P on the surface S of the heart H when the heart H does not dilate is the actual measurement distance L1. The rising amount ΔL represents a distance of (L0-L1), and is equal to or greater than a predetermined threshold value SH.

In Step ST7 in FIG. 7, control unit 100 illustrated in FIG. 4 drives the voice coil motor 60 by supplying power to the drive coil 59 of the voice coil motor 60 so that the actuator cylinder 61 is pushed in the direction X1. In this manner, the hydraulic fluid DL inside the actuator cylinder 61 is fed to the four actuator chambers 51 and 52 via the conduit 53 illustrated in FIG. 2. In Step ST8 in FIG. 7, increased pressure of the hydraulic fluid DL inside the actuator cylinder 61 causes the four actuator chambers 51 and 52 to extend in the direction Z2 (downward direction) as illustrated in FIG. 9. Accordingly, the movable suction unit 12 presses down the surface S (heart wall) of the heart H in the direction Z2 via the suction pads 21 and 22.

In this manner, in Step ST9 in FIG. 7, the position of the local site P1 on the surface S of the protruding heart H illustrated by the broken line, which is the measurement point, is pressed down in the direction Z2 to reach the position of the local site P as illustrated by the solid line. Therefore, the local site P1 of the surface S1 of the heart H when the heart H dilates, which is illustrated by the broken line, is lowered to the local site P of the surface S of the heart H when the heart H does not dilate, corresponding to the rising amount ΔL.

If the actual measurement distance L becomes equal to the target distance L0 or substantially equal to the target distance L0, the control unit 100 stops the operation of the actuator cylinder 61. If the operation of the actuator cylinder 61 is stopped, the pressure of the hydraulic fluid DL inside the actuator cylinder 61 is maintained, thereby stopping an operation in which the four actuator chambers 51 and 52 extend in the direction Z2. The rising amount ΔL is less than the predetermined threshold value SH.

In this way, based on the distance detection result of the displacement position detection unit 80, the control unit 100 can inhibit the position change in the height direction of the local site P of the operation site even though the heart H beats, since the operation of the four actuator chambers 51 and 52 of the position adjusting unit 50 causes the relative position of the local site P1 on the surface S1 of the heart H to be lowered with respect to the fixing base 11 of the support unit 10 in the direction Z2. Therefore, as illustrated in FIG. 10, the operator or the skilled person can easily connect the new graft vessel for the bypass 201 to the anastomosis opening G opened in the local site P of the heart H by using a thread F before a lesion appears in the stenosed coronary artery 200.

Incidentally, as illustrated in FIGS. 2 and 3, for example, when the off-pump coronary artery bypass has been completed, the conduit 53 for drive unit 55 can be detached from the connection terminal 54. In addition, the conduit 24 for suction unit 25 can be detached from the connection terminal 27. Then, the fixing base 11 can be detached from one end portion 20A of the fixing arm 20. In addition, if necessary, the support member 81 of the displacement position detection unit 80 can be preferably detached from the extension portion 15 of the fixing base 11.

In this manner, it is possible to use the fixing base 11 and the movable suction unit 12 of the new support unit 10 for the subsequent off-pump coronary artery bypass, after detaching the fixing base 11 and the movable suction unit 12 of the support unit 10 used once for the off-pump coronary artery bypass. In this manner, each time the operative procedure is performed, a new product can always be used as the disposable fixing base 11 and the disposable and movable suction unit 12 of the support unit 10 which comes into contact with the operation site. Accordingly, hygiene is taken into consideration.

Incidentally, during the off-pump coronary artery bypass, it could occur that an operator's hand blocks the laser light LT emitted from the displacement position detection unit 80 and the return light LR cannot return to the displacement position detection unit 80 side. In this case, the control unit 100 illustrated in FIGS. 1 and 2 gives an instruction to the drive unit 55, based on a value of the actual measurement distance L1 of previous heartbeat data of the heart H which is stored in the storage unit 110. Based on the value of the actual measurement distance L1 of the previous heartbeat data of the heart H, the drive unit 55 extends the actuator chambers 51 and 52. In this manner, if the actual measurement distance L1 becomes the target distance L0 or substantially the target distance L0, the control unit 100 illustrated in FIG. 4 stops the operation of the actuator cylinder 61 of the drive unit 55. In this manner, even in a case where the return light LR cannot temporarily return to the displacement position detection unit 80 side, the operation of the four actuator chambers 51 and 52 of the position adjusting unit 50 changes the relative position between the support unit 10 and the local site P on the surface S1 of the heart H. Accordingly, it is possible to inhibit the position change in the height direction of the local site P.

Second Embodiment

Figure 11:
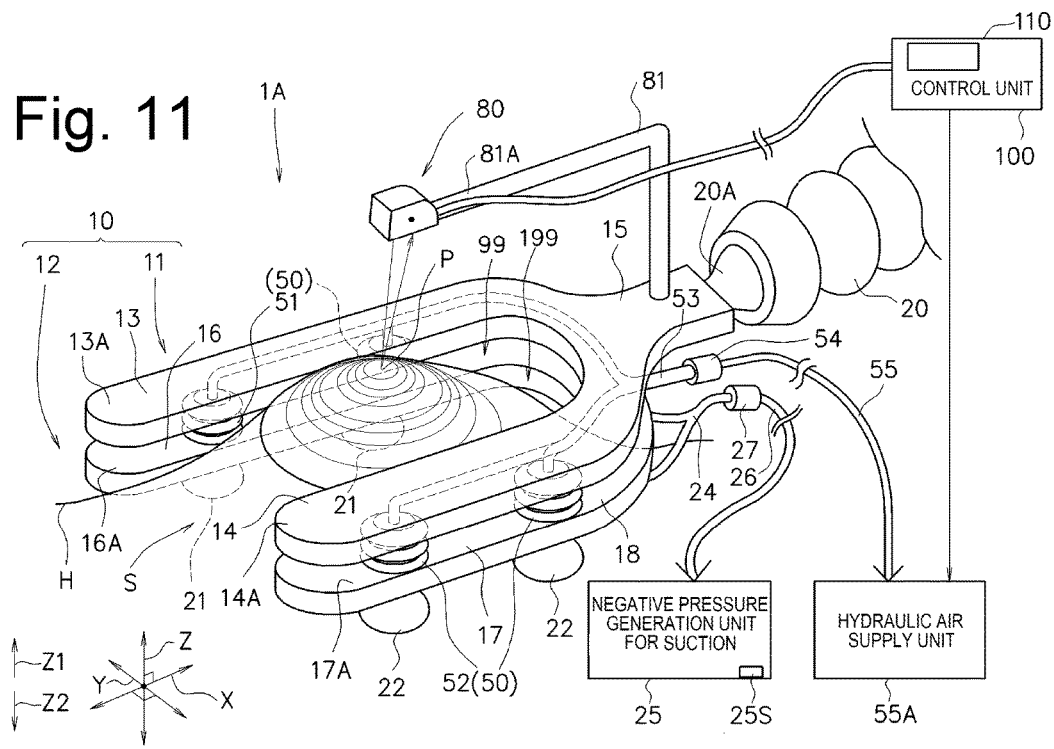
FIG. 11 is a perspective view illustrating a surgical fixing tool according to a second embodiment of the present invention.

FIG. 11 is a perspective view illustrating a surgical fixing tool 1A according to a second embodiment of the present invention. In a case where elements of the surgical fixing tool 1A according to the second embodiment of the present invention which are illustrated in FIG. 11 are substantially the same as the corresponding elements of the surgical fixing tool 1 according to the first embodiment of the present invention which are illustrated in FIG. 2, the same reference numerals will be given to the elements. Thus, description thereof will be cited, and repeated description will be omitted.

The surgical fixing tool 1A illustrated in FIG. 11 has the following point which is different from that of the surgical fixing tool 1 according to the present invention illustrated in FIG. 2.

In the surgical fixing tool 1 illustrated in FIG. 2, the drive unit 55 using the voice coil motor 60 increases the pressure of the hydraulic fluid for the actuator chambers 51 and 52, thereby extending the actuator chambers 51 and 52. In contrast, the surgical fixing tool 1A illustrated in FIG. 11 employs hydraulic gas such as hydraulic air instead of the hydraulic fluid. Therefore, the surgical fixing tool 1A employs a hydraulic air supply unit 55A, for example, instead of the drive unit 55.

The hydraulic air supply unit 55A extends the actuator chambers 51 and 52 in accordance with an instruction of the control unit 100. In this manner, if the actual measurement distance L1 becomes the target distance L0 or substantially the target distance L0, the control unit 100 stops the operation of the hydraulic air supply unit 55A. In this manner, the operation of the four actuator chambers 51 and 52 of the position adjusting unit 50 pushes down the local site P on the surface S of the heart H in the direction Z2. Accordingly, it is possible to inhibit the position change in the height direction of the local site P by changing the relative position between the support unit 10 and the local site P on the surface S of the heart H.

Third Embodiment

Figure 12:
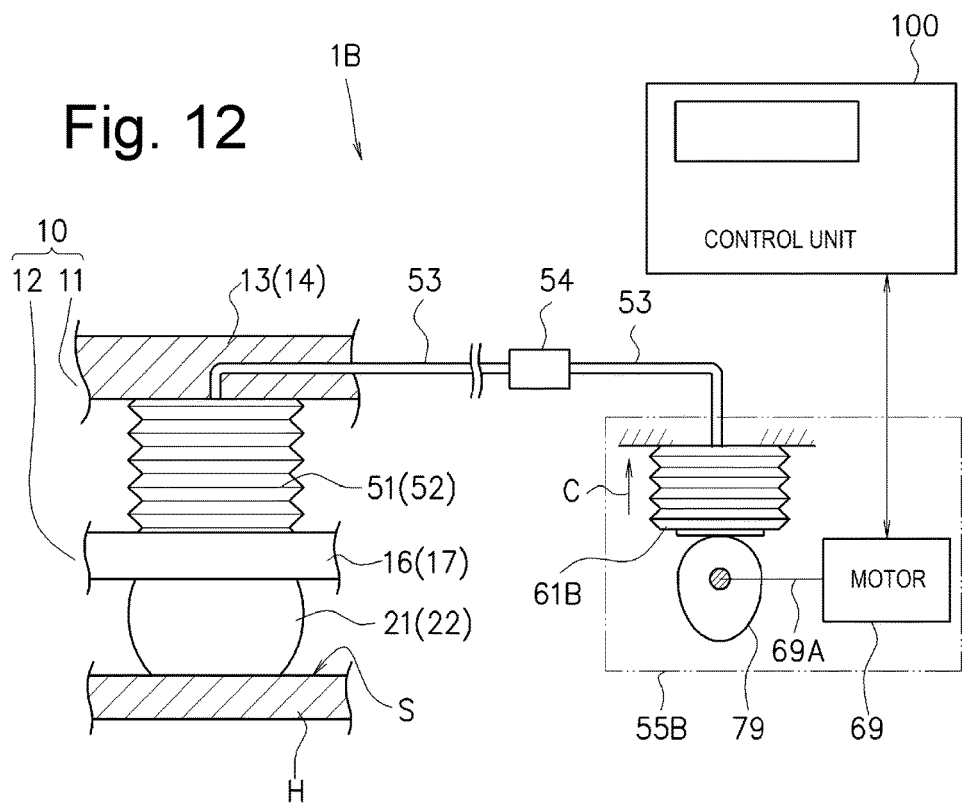
FIG. 12 is a side view illustrating a surgical fixing tool according to a third embodiment of the present invention.

FIG. 12 is a perspective view illustrating a surgical fixing tool 1B according to a third embodiment of the present invention. In a case where elements of the surgical fixing tool 1B according to the third embodiment of the present invention which are illustrated in FIG. 12 are substantially the same as the corresponding elements of the surgical fixing tool 1 according to the first embodiment of the present invention which are illustrated in FIG. 2, the same reference numerals will be given to the elements. Thus, description thereof will be cited, and repeated description will be omitted. The surgical fixing tool 1B illustrated in FIG. 12 has the following point which is different from that of the surgical fixing tool 1 according to the present invention illustrated in FIG. 2.

The surgical fixing tool 1B illustrated in FIG. 12 employs a hydraulic fluid supply unit 55B, for example, instead of the drive unit 55. The hydraulic fluid supply unit 55B has a bellows-shaped actuator cylinder 61B, a motor 69, and a rotary eccentric cam 79. The rotary eccentric cam 79 is attached to an output shaft 69A of the motor 69.

The control unit 100 drives the motor 69 so that the rotary eccentric cam 79 is rotated and pushed in a direction C. Therefore, the pressure of the hydraulic fluid inside the actuator chambers 51 and 52 increases so as to extend the actuator chambers 51 and 52. Accordingly, if the actual measurement distance L1 becomes the target distance L0 or substantially the target distance L0, the control unit 100 stops the operation of the hydraulic fluid supply unit 55B. In this manner, the operation of the four actuator chambers 51 and 52 of the position adjusting unit 50 pushes down the local site P on the surface S of the heart H in the direction Z2. Accordingly, it is possible to inhibit the position change in the height direction of the local site P by changing the relative position between the support unit 10 and the local site P on the surface S of the heart H.

Fourth Embodiment

Figure 13:
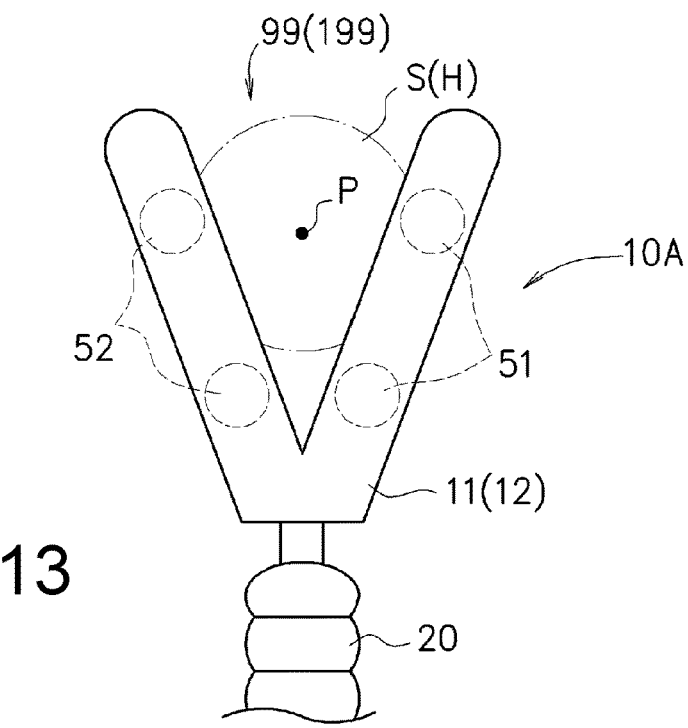
FIG. 13 is a plan view illustrating a support unit of a surgical fixing tool according to a fourth embodiment of the present invention.

FIG. 13 is a plan view illustrating a support unit 10A of a surgical fixing tool according to a fourth embodiment of the present invention. A structure of the support unit 10A illustrated in FIG. 13 is basically the same as a structure of the support unit 10 illustrated in FIG. 2. The fixing base 11 and the movable suction unit 12 of the support unit 10 illustrated in FIG. 2 have substantially U-shape when viewed from above. In contrast, the support unit 10A illustrated in FIG. 13 has a substantially V-shape when viewed from above. The support unit 10A has the opening portions 99 and 199.

Fifth Embodiment

Figure 14:
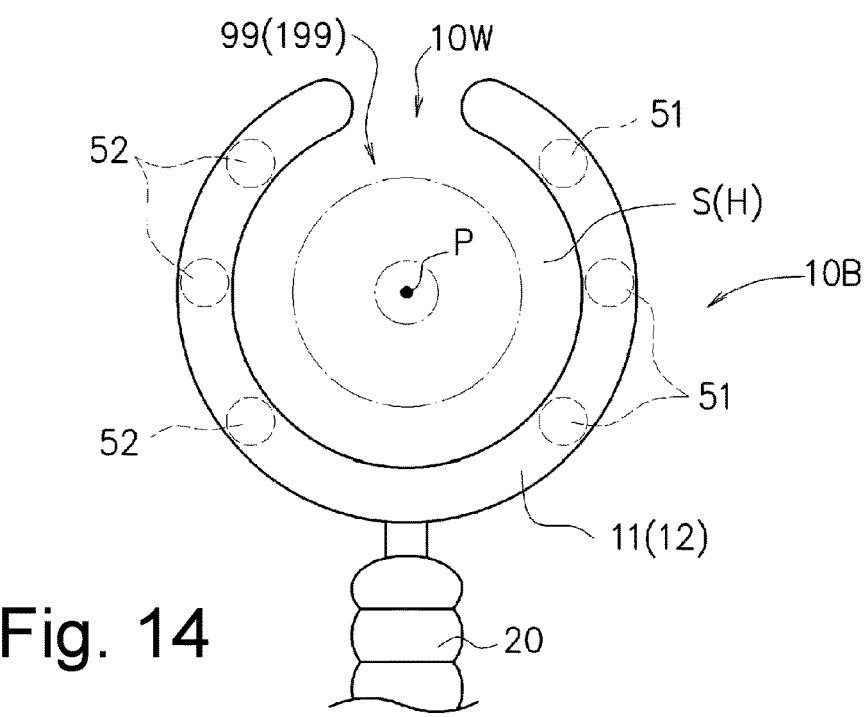
FIG. 14 is a plan view illustrating a support unit of a surgical fixing tool according to a fifth embodiment of the present invention.

FIG. 14 is a plan view illustrating a support unit 10B of a surgical fixing tool according to a fifth embodiment of the present invention. A structure of the support unit 10B illustrated in FIG. 14 is basically the same as the structure of the support unit 10 illustrated in FIG. 2. The support unit 10B illustrated in FIG. 14 has a substantially circular shape when viewed from above, and has a cutout portion 10W in a distal portion thereof. The support unit 10B has the opening portions 99 and 199.

Sixth Embodiment

Figure 15:
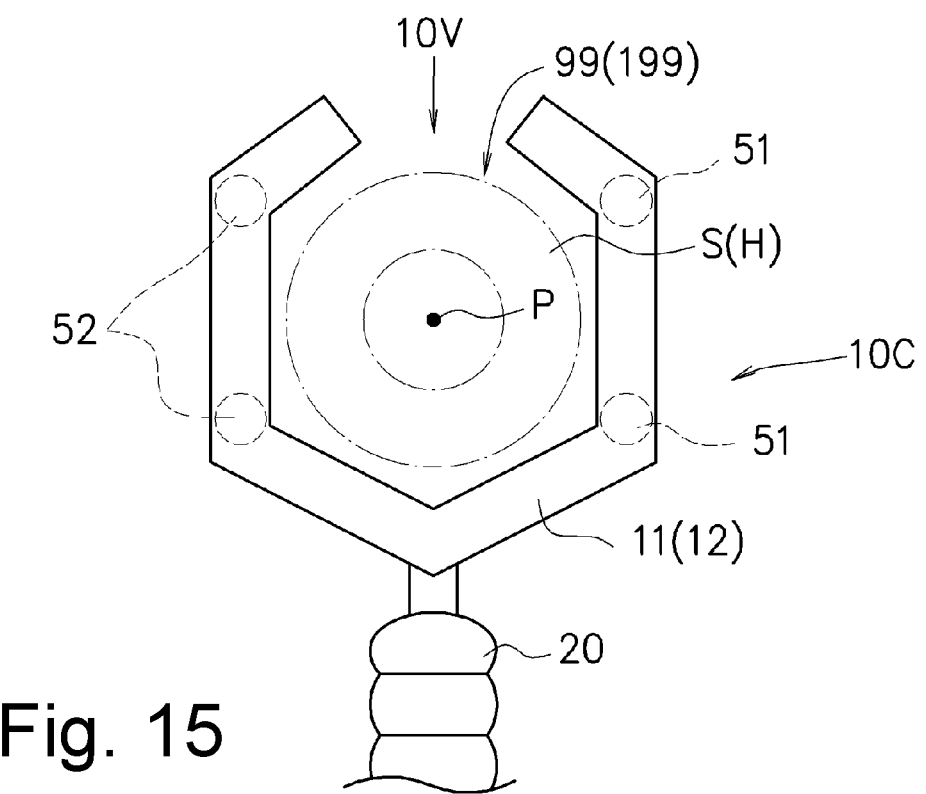
FIG. 15 is a plan view illustrating a support unit of a surgical fixing tool according to a sixth embodiment of the present invention.

FIG. 15 is a plan view illustrating a support unit 10C of a surgical fixing tool according to a sixth embodiment of the present invention. A structure of the support unit 10C illustrated in FIG. 15 is basically the same as the structure of the support unit 10 illustrated in FIG. 2. The support unit 10C illustrated in FIG. 15 has a polygonal shape (preferably hexagonal shape) when viewed from above, and has a cutout portion 10V in a distal portion thereof. The support unit 10C has the opening portions 99 and 199.

As described above, the surgical fixing tool 1 (1A or 1B) according to the embodiment of the present invention includes the support unit 10 which exposes a required area for the local site of the living body subjected to an operative procedure or operative skill and surrounds at least a portion of the local site so as to be contacted and fixed thereto. The surgical fixing tool 1 (1A or 1B) includes the position adjusting unit 50 that is disposed in the support unit 10, and that adjusts the relative position between the support unit 10 and the fixed living body local site, for example, the local site P on the surface S of the heart H, and the displacement position detection unit 80 that detects the displacement position where the living body local site is displaced in the height direction (direction Z), based on movements of the living body.

Then, based on the detection result of the displacement position in the height direction (direction Z) of the living body local site which is detected by the displacement position detection unit 80, the position adjusting unit 50 changes the relative position between the support unit 10 and the fixed living body local site, for example, the local site P on the surface S of the heart H, so as to inhibit the position change in the height direction (direction Z) of the living body local site.

According to this configuration, the support unit 10 exposes the area required for the living body local site P, and surrounds at least the portion of the local site P so as to be contacted and fixed thereto. Based on the detection result of the displacement position in the height direction of the living body local site which is detected by the displacement position detection unit 80, the position adjusting unit 50 changes the relative position between the support unit 10 and the fixed living body local site, for example, the local site P on the surface S of the heart H, thereby inhibiting the position change in the height direction of the living body local site P. Therefore, in a state where the peripheral portion on the surface of the living body such as the heart and the like is fixed by the support unit, the operation target site in the center of the peripheral portion on the surface of the living body such as the heart and the like is inhibited from moving along the height direction (direction Z) of the surface of the living body in response to movements of the living body. Accordingly, it is possible to easily and reliably perform treatment such as vascular anastomosis.

The support unit 10 has the opening portions 99 and 199 for exposing the living body local site, for example, the local site P on the surface S of the heart H. The support unit 10 has the fixing base 11, the fixing arm 20 which holds the position of the fixing base 11 for the fixing body (20D), and the movable suction unit 12 which has the suction pads 21 and 22 held in the lower portion of the fixing base 11 so as to perform suction on the surface of the living body. The suction pads 21 and 22 are connected to the negative pressure generation unit 25 which generates the negative pressure for the suction pads 21 and 22.

In this manner, the support unit 10 exposes the living body local site through the opening portions 99 and 199, thereby holding the position of the fixing base 11 with respect to the fixing body (20D) by using the fixing arm 20. The movable suction unit 12 performs suction on the surface of the living body by using the suction pads 21 and 22 in the lower portion of the fixing base 11. Therefore, while the support unit 10 holds the fixing body (20D) via the fixing arm 20 in a state where the support unit 10 is positioned on the surface of the living body, for example, the surface S of the heart H, the suction pads 21 and 22 of the movable suction unit 12 can perform the suction in a state where the surface S of the heart H which is the living body is stabilized.

The position adjusting unit 50 has the actuator chambers 51 and 52 which are the actuator members, and the drive unit 55 which feeds the hydraulic fluid to the actuator members. The actuator chambers 51 and 52 are disposed between the fixing base 11 and the movable suction unit 12. The drive unit 55 of the hydraulic fluid applies the pressure generated by the hydraulic fluid into the actuator chambers 51 and 52 so as to adjust the relative position between the fixing base 11 of the support unit 10 and the fixed living body local site, for example, the local site P on the surface S of the heart H, by changing the position of the movable suction unit 12 with respect to the fixing base 11.

In this manner, the drive unit 55 of the hydraulic fluid applies the pressure generated by the hydraulic fluid into the actuator chambers 51 and 52 so as to adjust the relative position between the fixing base 11 of the support unit 10 and the fixed living body local site, for example, the local site P on the surface S of the heart H, by changing the position of the movable suction unit 12 with respect to the fixing base 11. Therefore, the position of the movable suction unit 12 with respect to the fixing base 11 is changed so as to push the living body local site P. In this manner, it is possible to easily and reliably adjust the relative position between the fixing base 11 and the fixed living body local site, for example, the local site P on the surface S of the heart H.

The displacement position detection unit 80 is attached to the fixing base 11, and the displacement position detection unit 80 emits light LT to the living body local site exposed inside the support unit 10, for example, the local site P on the surface S of the heart H, so as to measure the actual measurement distance L1 between the fixing base 11 and the living body local site. After comparing the actual measurement distance L1 obtained from the displacement position detection unit 80 and the predetermined target distance L0 with each other, the drive unit 55 of the hydraulic fluid applies the pressure generated by the hydraulic fluid into the actuator chambers 51 and 52 so that the actual measurement distance L1 becomes the target distance L0, and accordingly the relative position is adjusted between the fixing base 11 of the support unit 10 and the fixed living body local site P by changing the position of the movable suction unit 12 with respect to the fixing base 11 of the support unit 10.

In this manner, the actual measurement distance L1 between the fixing base 11 of the support unit 10 and the living body local site P can be accurately obtained in a contactless manner, only by emitting the light LT to the living body local site, for example, the local site P on the surface S of the heart H, from the displacement position detection unit. The position of the movable suction unit 12 with respect to the fixing base 11 is changed so that the actual measurement distance L1 becomes the target distance L0. In this manner, it is possible to easily and reliably adjust the relative position between the fixing base 11 and the fixed living body local site P by pressing the living body.

The suction pads 21 and 22 and the negative pressure generation unit 25 are detachably connected, and the actuator chambers 51 and 52 serving as the actuator members and the drive unit 55 are detachably connected. In this manner, the suction pads 21 and 22 and the negative pressure generation unit 25 of the support unit 10 can be detached, and the actuator chambers 51 and 52 and the drive unit 55 of the support unit 10 can be detached. Accordingly, from a viewpoint of hygiene, the support unit used for an operative procedure can be detached from the negative pressure generation unit 25 and the drive unit 55. Therefore, a new support unit 10 can be attached and used for the subsequent operative procedure.

The fixing body for fixing the position of the fixing base 11 is a part of the operating table for holding the living body, for example, a rail 20D. In this manner, the fixing base 11 of the support unit 10 is fixed to the rail 20D by utilizing the rail 20D. Accordingly, the fixing base 11 of the support unit 10 can reliably hold a patient's living body local site P so as not to move.

The shape of the support unit 10 can employ any one of a U-shape, a V-shape, a substantially circular shape including an elliptical shape and an oval shape, and a polygonal shape. In this manner, in accordance with a shape of the living body or a shape of the operation target site, the shape of the support unit can employ any one of the U-shape, the V-shape, the circular shape, and the polygonal shape.

Without being limited to the above-described embodiments, the present invention can be modified in various ways within the scope not departing from the scope of Claims. The respective configurations of the above-described embodiments can be partially omitted, or can be optionally combined with each other so as to adopt different configurations.

In the above-described embodiments according to the present invention, the surgical fixing tool is attached to the heart surface by means of suction, and is used when movement of the heart is limited in only a portion on the heart surface fixed by the suction. However, without being limited thereto, the surgical fixing tool according to the present invention can be applied to a case where the position change in the height direction of the local site is inhibited by exposing the area required for other living body local sites in addition to the heart surface subjected to the operative procedure or the operative skill and surrounding, attaching, and fixing at least a portion of the local sites.

As the displacement position detection unit 80, a laser displacement sensor of a triangulation system using laser light is used. However, without being limited thereto, other types of sensor may be used so as to detect the displacement position where the local site is displaced in the height direction, based on living body movements.

As an example, the position adjusting unit 50 includes the four actuator chambers 51 and 52, and the movable suction unit 12 includes the four suction pads 21 and 22. However, without being limited thereto, a configuration can also be adopted which includes three or less or five or more actuator chambers and suction pads.

As the living body local site subjected to the operative procedure or the operative skill, the local site P on the surface S of the heart wall of the heart H has been described as an example. However, without being limited thereto, the living body local site subjected to the operative procedure or the operative skill may be other organs which move in response to living body movements.

What is claimed is:

1. A surgical fixing tool comprising:
a frame adapted to circumscribe a target area for a living body local site to be subjected to an operative procedure, the frame having a fixed portion and a movable portion, wherein the movable portion is configured to attach to the living body local site;
a position adjuster disposed in the frame and that is configured to adjust a relative position between the fixed portion and the movable portion; and
a displacement position detector on the fixed portion that is configured to detect a displacement position where the living body local site is displaced in a height direction, wherein the detection of the displacement position is based on movements of the living body,
wherein, based on a detection result of the displacement position in the height direction of the living body local site which is detected by the displacement position detector, the position adjuster is configured to change the relative position between the fixed and movable portions of the frame so as to inhibit a relative position change in the height direction between the living body local site and the fixed portion of the frame,
wherein the frame defines an opening portion for exposing the living body local site,
wherein the fixed portion of the frame comprises a fixing base and a fixing arm extending from the fixing base to hold a position of the fixing base with respect to a stationary body, and the movable portion of the frame comprises a movable arm supporting a suction pad, wherein the suction pad is held in a lower portion of the moveable arm so as to perform suction on a surface of the living body,
wherein the suction pad is adapted to be connected to a negative pressure generator which generates negative pressure for the suction pad,
wherein the position adjuster comprises an actuator and a driver which is configured to feed a hydraulic fluid to the actuator member,
wherein wherein the actuator is disposed between the fixing base and the movable arm, and
wherein the driver of the hydraulic fluid is configured to apply pressure generated by the hydraulic fluid into the actuator so as to adjust the relative position between the fixing base of the frame and the living body local site by changing a position of the movable arm with respect to the fixing base of the frame.

2. The surgical fixing tool according to claim 1, wherein the displacement position detector is attached to the fixing base,
wherein the displacement position detector is configured to emit light to the living body local site exposed inside the frame so as to measure a distance between the fixing base and the living body local site, and
wherein after comparing an actual measurement distance obtained from the displacement position detector and a predetermined target distance with each other, the driver of the hydraulic fluid is configured to apply the pressure generated by the hydraulic fluid into the actuator so that the actual measurement distance becomes the target distance, and accordingly the relative position is adjusted between the fixing base of the frame and the living body local site by changing the position of the movable arm with respect to the fixing base of the frame.

3. The surgical fixing tool according to claim 1, wherein the suction pad and the negative pressure generator are detachably connected to each other, and the actuator and the driver are detachably connected to each other.

4. The surgical fixing tool according to claim 1, wherein the fixing arm is adapted to attach to an operating table which holds the living body.

5. The surgical fixing tool according to claim 1, wherein a shape of the frame is selected from a group comprising a U-shape, a V-shape, a substantially circular shape, an elliptical shape, an oval shape, and a polygonal shape.

* * * * *